United States Patent [19]
Vincent

[11] Patent Number: 5,601,604
[45] Date of Patent: Feb. 11, 1997

[54] UNIVERSAL GASTRIC BAND

[75] Inventor: Vernon L. Vincent, Santa Barbara, Calif.

[73] Assignee: Inamed Development Co., Caranteria, Calif.

[21] Appl. No.: 68,411

[22] Filed: May 27, 1993

[51] Int. Cl.[6] .................................................. A61B 17/00
[52] U.S. Cl. .......................................... 606/216; 606/228
[58] Field of Search ..................... 606/157, 148, 606/216, 228; 128/899, 898, 780; 24/16

[56] References Cited

U.S. PATENT DOCUMENTS

| | | | |
|---|---|---|---|
| 3,577,601 | 4/1971 | Mariani et al. | 24/16 PP |
| 4,416,267 | 11/1983 | Garren et al. | 128/898 |
| 4,592,339 | 6/1986 | Kuzmak et al. | 128/899 |
| 4,696,288 | 9/1987 | Kuzmak et al. | 128/780 |
| 4,813,416 | 3/1989 | Pollack et al. | 606/216 |
| 5,074,868 | 12/1991 | Kuzmak | 606/157 |
| 5,160,338 | 11/1992 | Vincent | 606/228 |
| 5,207,694 | 5/1993 | Broomé | 606/148 |

*Primary Examiner*—Michael Powell Buiz
*Attorney, Agent, or Firm*—Michael G. Petit

[57] ABSTRACT

A gastric band for placement around the stomach is described which is useful for the treatment and control of morbid obesity. The gastric band has an inner surface and an outer surface. The inner surface has an inflatable member disposed thereon which substantially completely covers the inner surface of the band. A remote fill port is in fluid communication with the interior of the inflatable member. The gastric band is invasively placed in an encircling position around the stomach by the facile closure of a single fastening means. After the band is fastened around the stomach, a fluid is injected into the inflatable member thereby constricting the stoma of the stomach. Preferably, measuring means situated within the stomach provides a measure of the stoma opening. The inflatable member is adjusted so that the stoma opening is at the desired diameter. The advantage of the present gastric band over prior art bands is that adjustment of the tensioning the band prior to inflation is not required inasmuch as the latitude for inflation provided by the enlarged inflatable member enables a versatile range of adjustment.

1 Claim, 1 Drawing Sheet

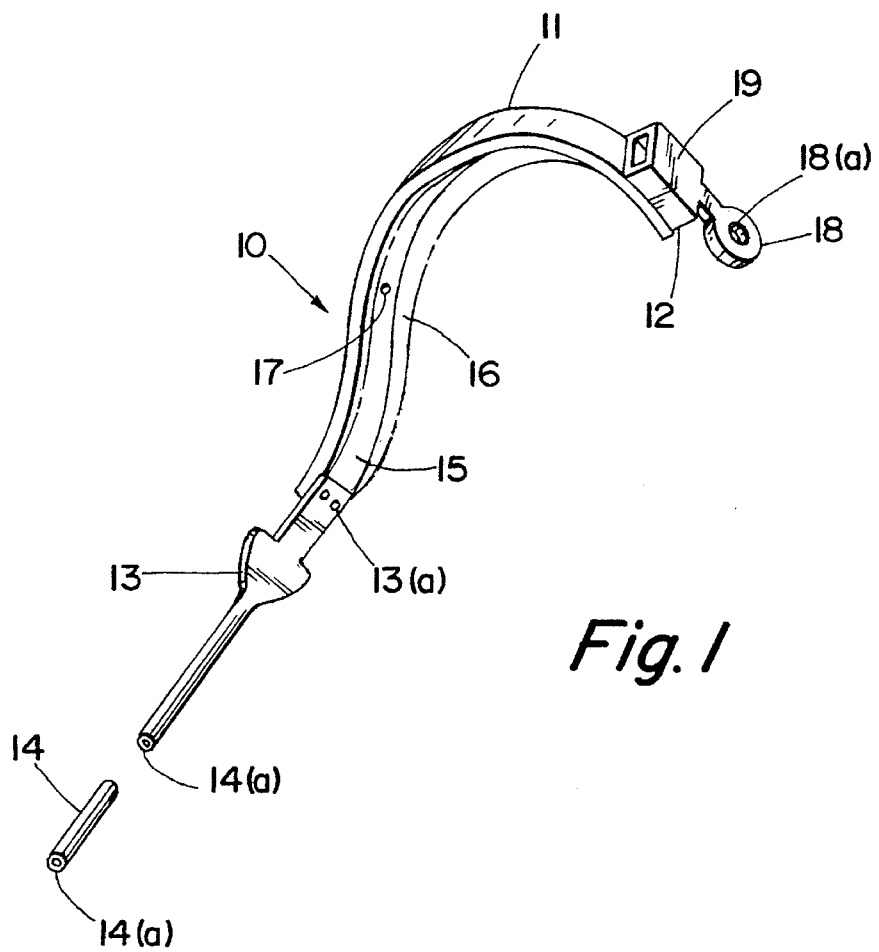
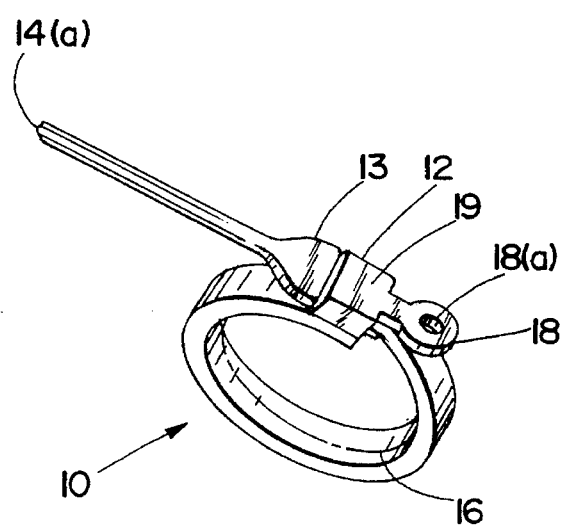

UNIVERSAL GASTRIC BAND

BACKGROUND OF THE INVENTION

1. Field of the Invention

This invention relates to devices for the control of obesity, and, more particularly, to a surgically implantable adjustable band for encircling the stomach.

2. Prior Art

Several years ago, Kuzmak, et al. in U.S. Pat. 4,592,339, incorporated herein by reference, described a belt-like band for encircling the stomach to control morbid obesity. The band comprised substantially a belt which could be passed around the stomach in a circling position and then cinched tight in order to adjust the stoma opening within the stomach. Further improvements in the gastric band have included having an adjustable portion of the band comprising an inflatable member which permits the fine adjustment of the stoma opening after the size of the stoma is initially set by the band tightening procedure. The band tightening procedure normally involves the placement of a calibrating apparatus in the stomach to detect the stoma size. Once the apparatus is placed within the stomach the gastric band is cinched down tight until the stoma opening approximates the desired size. The band is fastened in position, usually by sutures, and the stoma opening finally adjusted by injecting a fluid into an inflatable member which is coextensive with a portion of the inner stomach-contacting surface of the band. The means for injecting the fluid into the inflatable member usually comprises a fill port located beneath the skin which can be accessed extracorporeally by transdermal injection. Thus, following implantation, the gastric band can be adjusted, within a narrow range, to enlarge or reduce the stoma as required.

One of the disadvantages of the prior art gastric bands is the difficulty in tensioning the band around the stomach to approximate the desired stoma. This is particularly difficult when the band is to be placed laparoscopically. When the band is placed laparoscopically, special instruments are required to tension the band prior to the fine adjustment of the stoma. Such instruments as are required to grasp the band and pull it into an encircling position around the stomach then cinch it tight, are difficult to manipulate through a laparoscopic canula. It would therefore be desirable to provide a band having an inflatable member thereon which can be easily fastened into an encircling position around the stomach and in which the final adjustment of the stoma opening can be regulated solely by the injection of fluid into the inflatable member.

SUMMARY OF THE INVENTION

An object of this invention is to provide a gastric band which can be easily placed and fastened into an encircling position around the stomach laparoscopically.

It is yet another object of this invention to provide a gastric band wherein the band can be easily affixed in an encircling position around the stomach by conventional laparoscopic instruments.

It is yet another object of this invention to provide a gastric band adapted for laparoscopic placement around the stomach thereafter to compress the encircled portion of the stomach to constrict the stoma thereof which constriction may be adjusted entirely by means of an inflatable member.

These and other objects of this invention will soon become apparent as we turn now to the preferred embodiments.

BRIEF DESCRIPTION OF THE DRAWINGS

FIG. 1 is a perspective view of the gastric band according to the present invention.

FIG. 2 is the gastric band according to the present invention fastened in an encircling position and partially inflated.

DESCRIPTION OF THE PREFERRED EMBODIMENT

As mentioned earlier, prior art gastric bands have two steps or stages of adjustment: the first step roughly affixes the gastric band in a position to encircle the stomach with the stoma opening approximating the desired size. This first adjustment is analogous to tightening a belt around the waist until the buckle tongue passes through a hole rendering comfortable tension. The next step in the adjustment requires injection of a fluid into the inflatable member to bring the stoma opening to the desired size.

Prior art gastric bands, lacking a large range of inflatable adjustment, require initial tensioning. The first step in the sizing process requires tensioning the band, and holding the tension on the band, while sutures are placed to lock the band in the encircling position. This is a cumbersome procedure to perform laparoscopically and the present invention overcomes some of the difficulties with tensioning the band.

Turning now to FIG. 1, we see a gastric band, generally indicated at the numeral 10, which has a body portion 11 with an inner stomach-facing surface 15. The body portion 11 has a head end 12 and a tail end 13 with one or more suture holes 13(a) therein. A fill tube 14, which is generally a tube having a single lumen 14(a) coextensive therewith, is in fluid communication with an inflatable member 16 on the inner surface 15 of the band body 11. It is an important feature of this invention that the inflatable portion 16 is substantially co-extensive with the inner surface 15 of the body portion 11. The central lumen 14(a) of the fill tube 14 enters into the inflatable member 16 at lumen opening 17. The head 12 of the body portion 11 has a buckle 19 with a pull tab 18 having a suture hole 18(a) integral therewith. Both Portions which receive a suture, that is the buckle 19 with the pull tab 18 and the tail 13, are preferably reinforced with dacron.

In practice, the gastric band is placed in the circling position around the stomach as shown in FIG. 2. (In FIG. 2 the stomach is omitted for clarity.) This is accomplished by pushing the fill tube 14 through a laparoscopic canula (not shown) in the patient's abdomen. Laparoscopic placement consists of blunt dissection around the greater curvature of the stomach. The end of the fill tube 14 is passed around the stomach, and the tail 13 is attached to the buckle 19, so that the buckle and the tail are irreversibly affixed to one another. In this sense, the band is a "one-size-fits-all" device. That is, for a particular band there is only one single position in which the tail and buckle can be attached to one another. The adjustment of the stoma; the narrow opening in the stomach created by the band, is calibrated by a second step after the band is secured in this single position. Prior art gastric band employ an adjustable balloon portion that is used for small post-operative adjustment of the stoma if necessary. The laparoscopic hydraulic gastric band outlined herein has a larger balloon covering a greater area of the internal diameter of the gastric band. The inflatable member or balloon 16 preferably is coextensive with the inner stomach-facing surface 15 of the band between the head end 12 and the tail end 13. This larger balloon is utilized to adjust the stoma at the time of surgery. The interior of the adjustable balloon 16 is in fluid communication with the injection reservoir (not shown) by means of the central lumen 14(*a*) of the fill tube 14, as with prior art adjustable gastric bands. The inflatable member 16 is gradually inflated with saline via the injection reservoir (not shown) such that the inflatable member 16, which, as stated above, is coextensive with the inner surface 15 of the band 11 between the head end 12 and the tail end 13, presses on and constricts the stomach wall underlying the band. This results in the decrease of the opening (stoma) inside the stomach directly under the encircling band.

An electronic pressure transducer known as a gastrostenometer electronic sensor, coupled to a calibration probe known generically as a "calibration tube" is used to measure the size of the stoma. The calibration tube is introduced through the patient's mouth and esophagus into the stomach. The band is inflated, tightening it around the tip of the calibration tube. The gastrostenometer electronic sensor indicates the stoma diameter created as the band is tightened.

The present invention allows for the laparoscopic implantation of a therapeutic surgical device without the risks associated with major abdominal incisions in the obese patient. Faster healing, reduced complications, reduced hospital stay and drastically reduced pain are among the advantages of laparoscopic placement. The gastric band according to the present invention facilitates laparoscopic placement and will also allow wider use of the gastric band system to create a gastric restricter procedure for the treatment of morbid obesity. This band enables more surgeons, skilled in the art of laparoscopic surgery to undertake this operation without the need for highly specialized, difficult to use tensioning instruments. Since there is only one locking position for the band around the stomach, the procedure itself should lend itself to more rigorous standardization. Also, more patients will consider having this procedure performed because of the advantages of laparoscopic surgery over traditional abdominal laparotomies. These advantages, coupled with the advantages of the prior art gastric bands, which enable post operative fine tuning of the stoma, enable a more facile procedure to be performed.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A gastric band for the treatment of morbid obesity, said band being adapted for laparoscopic placement around the stomach of a patient, said band comprising a body portion having a head end and a tail end and an inner stomach-facing surface therebetween, said tail end comprising an elongate tubular member having means thereon for providing a fluid tight connection of said tubular member to an injection reservoir, said head end having means thereon for receiving said tail end and locking said band into a circle having an inner diameter and an inflatable member substantially entirely coextensive with said inner stomach-facing surface of said body portion of said gastric band when said band is locked into said circle having said inner diameter, and which said inflatable member is in fluid communication with said tubular member.

* * * * *